(12) United States Patent
Lee et al.

(10) Patent No.: US 11,246,499 B2
(45) Date of Patent: Feb. 15, 2022

(54) FAR-INFRARED EMITTERS WITH PHYSIOLOGICAL SIGNAL DETECTION AND METHOD OF OPERATING THE SAME

(71) Applicants: National Taiwan University of Science and Technology, Taipei (TW); Taipei Medical University, Taipei (TW)

(72) Inventors: San-Liang Lee, Taipei (TW); Chao-Hsiung Tseng, New Taipei (TW); Ling-Hsiu Hung, New Taipei (TW); Yung-Ho Hsu, Taipei (TW); Cheng-Hsien Chen, Taipei (TW)

(73) Assignees: NATIONAL TAIWAN UNIVERSITY OF SCIENCE AND TECHNOLOGY, Taipei (TW); TAIPEI MEDICAL UNIVERSITY, Taipei (TW)

( * ) Notice: Subject to any disclaimer, the term of this patent is extended or adjusted under 35 U.S.C. 154(b) by 211 days.

(21) Appl. No.: 16/681,152

(22) Filed: Nov. 12, 2019

(65) Prior Publication Data
US 2020/0178822 A1 Jun. 11, 2020

(30) Foreign Application Priority Data
Dec. 6, 2018 (TW) .................................. 107143988

(51) Int. Cl.
*A61B 5/024* (2006.01)
*A61B 5/00* (2006.01)

(52) U.S. Cl.
CPC ........ *A61B 5/02416* (2013.01); *A61B 5/0004* (2013.01); *A61B 5/7271* (2013.01); *A61B 5/7203* (2013.01)

(58) Field of Classification Search
CPC . A61B 5/0004; A61B 5/0059; A61B 5/02416; A61B 5/02438; A61B 5/0265; A61B 5/0507; A61B 5/113; A61B 5/7203; A61B 5/7271; A61B 5/746; A61N 5/06–2005/073; A61F 7/00–2007/126
See application file for complete search history.

(56) References Cited

U.S. PATENT DOCUMENTS

| 7,811,234 | B2 * | 10/2010 | McGrath ................... A61B 5/08 600/508 |
| 11,000,188 | B2 * | 5/2021 | Farahbakhshian ........................... A61B 5/02116 |
| 2008/0045832 | A1 * | 2/2008 | McGrath ................ A61B 5/024 600/427 |
| 2020/0178807 | A1 * | 6/2020 | Farahbakhshian ..... A61B 5/015 |

* cited by examiner

*Primary Examiner* — Jonathan T Kuo
(74) *Attorney, Agent, or Firm* — WPAT, PC

(57) ABSTRACT

A far-infrared emitters with physiological signal detection and method of operating the same is disclosed. A far-infrared beam module is switched on and generates far-infrared beam irradiating to a human body when a control unit starting up a microwave detecting module detecting physiological signal of the human body. The control unit is switched off when the time that the far-infrared beam irradiating on the human body reach a presetting period of time, thereby achieving the purpose of energy conservation.

13 Claims, 4 Drawing Sheets

FAR-INFRARED EMITTERS WITH PHYSIOLOGICAL SIGNAL DETECTION AND METHOD OF OPERATING THE SAME

CROSS REFERENCE TO RELATED APPLICATION

This application also claims priority to Taiwan Patent Application No. 107143988 filed in the Taiwan Patent Office on Dec. 6, 2018, the entire content of which is incorporated herein by reference.

FIELD OF THE INVENTION

The present invention relates to a far-infrared emitter with physiological signal detection and the method of operating the same, and more particularly, to an emitter that is highly sensitive, low cost, small in size with great portability, and is specifically configured with a far-infrared module which can be turn off according to the detection of a physiological signal from a user for energy saving.

BACKGROUND OF THE INVENTION

Far infrared (FIR) is an electromagnetic wave with a wavelength ranged between 760 nm and 1 mm that is ranged between the wavelength of microwave and that of visible light. Specifically, far infrared is often defined as an invisible light with a wavelength larger than that of red light. Generally, thermal radiation emitted by all objects under room temperature is an electromagnetic wave in this far infrared wavelength range. The detection of thermal radiation can be applied in various fields, including industry, military, science and medication, etc. For instance, it can be used in a thermal imaging device for detecting the temperature distribution of a heat-emitting object so as to be used in an infrared intensity analysis and thus to be displayed as a thermal image.

Recent years, with the increasing environmental conscience, FIR detection is being used in various environmental tests, such as gas detection and water pollution detection. Generally according to wavelength, the wavelength of near infrared is ranged between 0.7 μm and 2 μm, the wavelength of medium infrared is ranged between 3 μm and 5 μm, and wavelength of far infrared is ranged between 6 μm and 8 μm. According to many recent medical researches, the far-infrared radiation devices can transfer energy purely in the form of heat so as to be perceived by organisms for achieving blood circulation improvement, metabolism promotion and tissue regeneration enhancement, and so on.

Therefore, there are many far infrared therapy devices currently available that are to be used for eliminating fatigue, improving blood circulation and relieving muscle ache. However, those conventional far infrared therapy devices are only configured with basic on/off control and simply radiation intensity adjustment that it is generally lack on any biological signal detection ability. Moreover, as those conventional far infrared therapy devices are usually made of far infrared ceramics or far infrared carbon fiber heating panels that can be very energy inefficient and can generate high temperature, it can cause great energy waste when it is operating without deliberative human supervision and also may cause thermal skin injury to uncareful personnel.

Therefore, it is in need of an emitter that is highly sensitive, low cost, small in size with great portability, and is specifically configured with a far-infrared module which can be turn off according to the detection of a physiological signal from a user for energy saving.

SUMMARY OF THE INVENTION

In an embodiment, the present invention provides a far-infrared emitter with physiological signal detection, which comprises:
a microwave detecting module, further comprising: a self-injection-locked-state oscillating integrated antenna and a demodulator, for emitting an oscillating signal to a human body so as to receive a reflection signal reflected back from the human body and thus acquiring a physiological signal of the human body accordingly;
a far-infrared beam module, for generating a far-infrared beam; and
a control unit, electrically connected to the microwave detecting module and the far-infrared beam module, to be used for activating the microwave detecting module for detecting the physiological signal of the human body continuously while thereafter activating the far-infrared beam module to radiate the far-infrared beam onto the human body.

In an embodiment, the present invention provides a method of operating the far-infrared emitter with physiological signal detection, which comprises the steps of:
(a) activating a control unit;
(b) enabling the control unit to activate a microwave detecting module, which further comprises: a self-injection-locked-state oscillating integrated antenna and a demodulator, for enabling the microwave detecting module to emit an oscillating signal to a human body so as to receive a reflection signal reflected back from the human body and thus to acquire a physiological signal of the human body accordingly;
(c) determining whether there is any physiological signal of the human body being detected by the microwave detecting module; if so, the flow proceeds to step (d); otherwise, an alerting procedure is being initiated;
(d) enabling the control unit to activate a far-infrared beam module for generating a far-infrared beam to be projected onto a human body while enabling the microwave detecting module to perform the detection of the physiological signal of the human body continuously;
(e) determining whether the irradiation period of the far-infrared beam onto the human body had reached a presetting period of time or not; if so, the flow proceeds to step (f); otherwise, the flow proceeds back to step (d) until the radiation of the far-infrared beam had reached the presetting period of time; and
(f) turning off the control unit.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
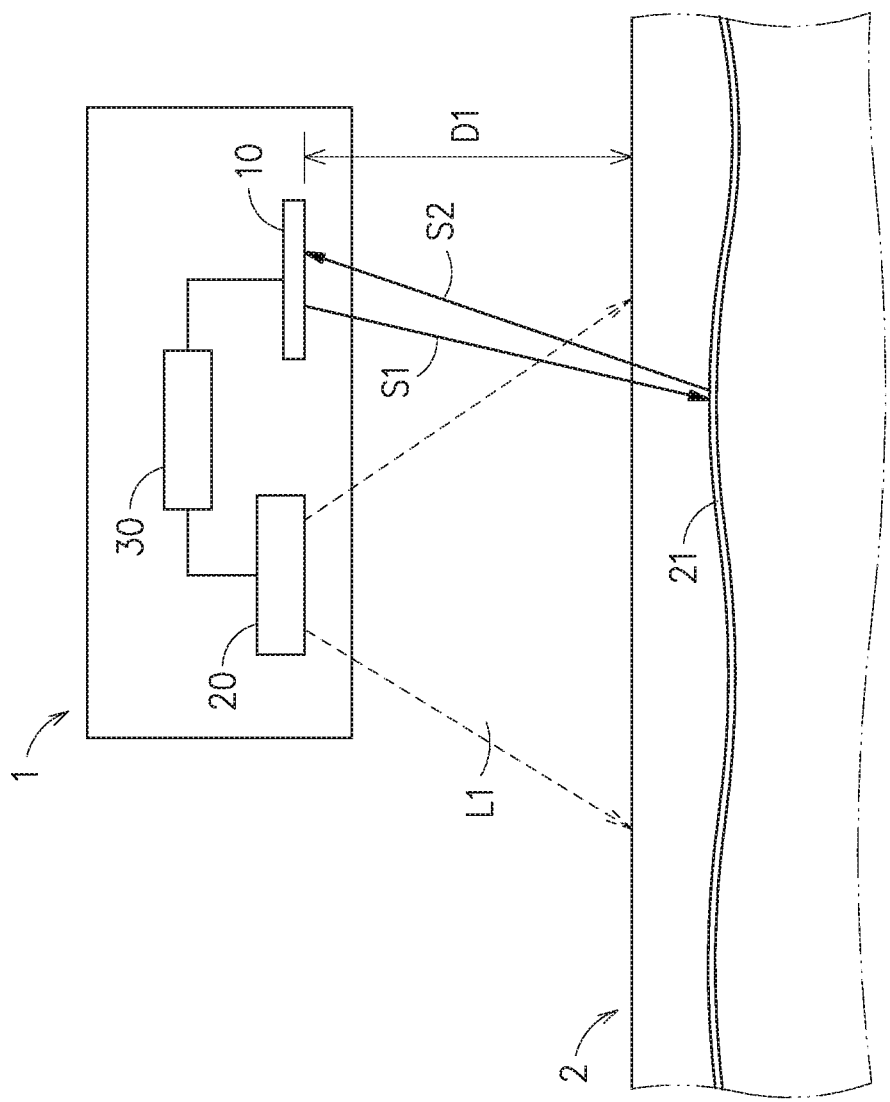
FIG. 1 is a schematic diagram showing a far-infrared emitter with physiological signal detection according to an embodiment of the present invention.

Please refer to FIG. 1, which is a schematic diagram showing a far-infrared emitter with physiological signal detection according to an embodiment of the present invention. In FIG. 1, a far-infrared emitter with physiological signal detection 1 is disclosed, which comprises: a microwave detecting module 10, a far-infrared beam module 20 and a control unit 30.

The microwave detecting module 10 is used for emitting an oscillating signal S1 to a human body 2 so as to receive a reflection signal S2 reflected back from the human body 2 and thus acquiring a physiological signal of the human body 2 accordingly. It is noted that the physiological signal can include signals of vascular pulsation, heartbeat or respiration, and in the embodiment of FIG. 1, the physiological signal show the pulsation detection of a vessel 21. The oscillating signal S1 is a CW (continuous wave) oscillating signal of micro wave with single oscillation frequency or a modulating frequency.

Figure 2:
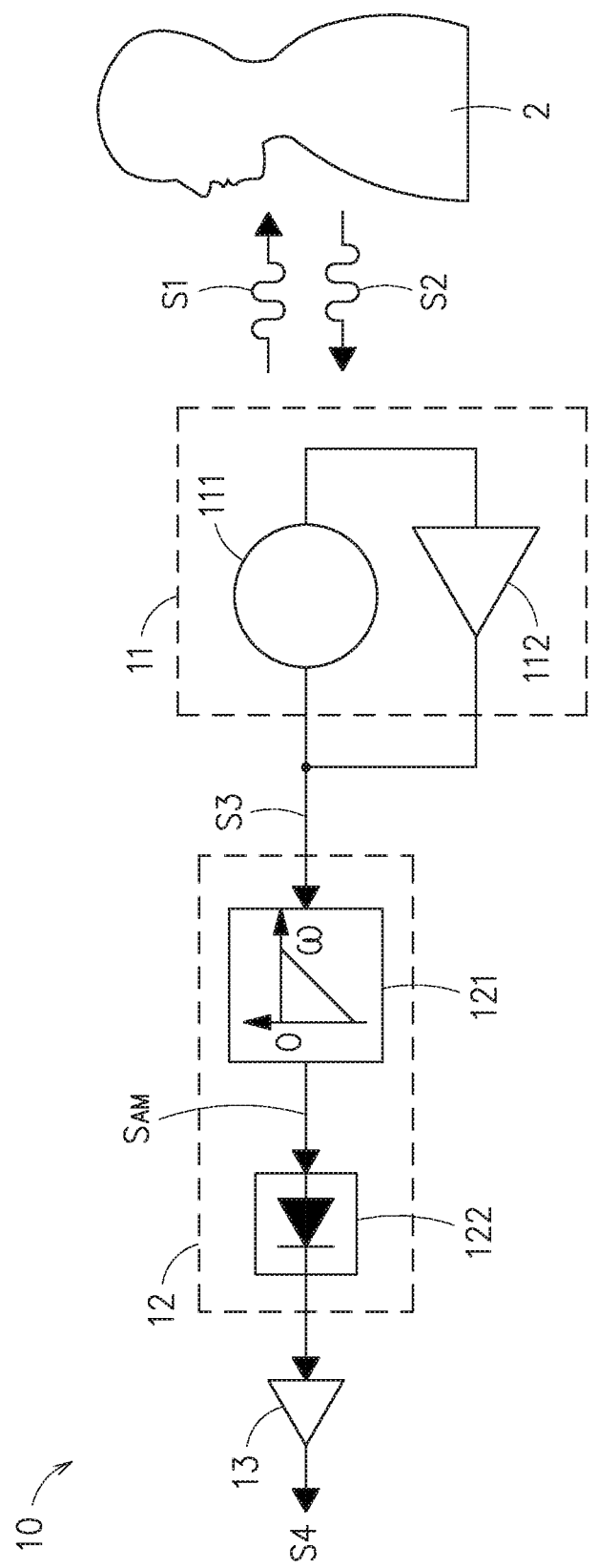
FIG. 2 is a schematic view of a microwave detection module according to an embodiment of the present invention.

Please refer to FIG. 2, which is a schematic view of a microwave detection module according to an embodiment of the present invention. In FIG. 2, the microwave detecting module 10 further comprises: a self-injection-locked-state oscillating integrated antenna 11 and a demodulator 12. Moreover, the self-injection-locked-state oscillating integrated antenna 11 is further configured with an antenna 111 and an active unit 112 in a manner that the active unit 112 is electrically connected to the antenna 111, whereby, the antenna 111 is enabled to perform a frequency selection operation while being enabled to oscillate with the active unit 112 so as to generate the oscillating signal S1 that is then to be transmitted to the human body 2 by the antenna 111, and as the oscillating signal S1 is substantially a radio frequency signal that can be projected and cover the projection area of the far infrared beam L1 so as to modulate the physiological movement of the human body 2, the corresponding modulation of the physiological movement is reflected back as a reflection signal S2 from the human body 2 so as to be received by the antenna 111. Thereby, the self-injection-locked-state oscillating integrated antenna 11 will be conditioned and locked into a self-injection-locked state, enabling the frequency of the oscillating signal to offset and thus to be modulated into a frequency modulation/amplitude modulation signal S3. Moreover, the demodulator 12 is used for receiving the frequency modulation signal/amplitude modulation signal S3 and then demodulating the frequency modulation signal/amplitude modulation signal S3 so as to acquire the physiological signal S4 of the human body 2. In this embodiment, the demodulator 12 is electrically connected to a base band amplifier 13 and us used for receiving and amplifying the physiological signal S4.

In the embodiment shown in FIG. 2, the demodulator 120 further comprises: a differentiator 121 and an envelope detector 122. The differentiator 121 is electrically connected to the self-injection-locked-state oscillating integrated antenna 11 for receiving the frequency modulation signal/amplitude modulation signal S3 to be used in a differential operation for converting the frequency modulation component of the signal S3 into an amplitude modulation component so as to convert the frequency modulation/amplitude modulation signal S3 into an amplitude modulation signal $S_{AM}$, by that the microwave detecting module 10 is enabled to become more sensitive to the physiological signs of the human body 2. In addition, the envelope detector 122 that is electrically connected to the differentiator 12 for receiving the amplitude modulation signal $S_{AM}$ is used for performing an amplitude demodulation operation upon the amplitude modulation signal $S_{AM}$ so as to acquire the physiological signal S4. In this embodiment, the differentiator 121 is further being used for converting the frequency modulation into the amplitude modulation so as to be integrated with the frequency/amplitude modulation of the oscillating signal S1 that is affected by the physiological signs of the human body 2, by that the microwave detecting module 10 is enabled to become more sensitive to the physiological signs of the human body 2

It is noted that the microwave detecting module 10 shown in FIG. 2 is only an embodiment, and thus the present invention is not limited thereby. In other embodiments, the demodulator 12 can simply be an envelope detector, or can be other device that can be referred from those disclosed in TW patent appl. No. 106143627, "NON-CONTACT SELF-INJECTION-LOCKED SENSOR".

As the far-infrared beam module 20 shown in FIG. 1, it is used for generating a far-infrared beam L1 so that it can be made of a material capable of generating a far-infrared beam by heating the same, which can be a semiconductor wafer, a ceramic substrate, a coil/filament, a MEMS chip, a carbon fiber; and thus the far-infrared beam module 20 can be a far-infrared light emitting diode or a far-infrared laser, but it is not limited thereby.

The control unit 30 is electrically connected to the microwave detecting module 10 and the far-infrared beam module 20 that it is to be used for activating the microwave detecting module 10 for detecting the physiological signal of the human body 2 continuously while thereafter activating the far-infrared beam module 20 to radiate the far-infrared beam L1 onto the human body 2. The activation of the control unit 30 can be performed either by the use of an application program or a button, and moreover, the application program can be designed to be installed on any cell phone.

In addition, the present invention further defined an effective detection distance D1 between the microwave detecting module 10 and the human body 2, and when the distance between the microwave detecting module 10 and the human body 2 is within the range of the effective detection distance D1, the microwave detecting module 10 is able to detect the physiological signal of the human body 2. That is, when the distance between the microwave detecting module 10 and the human body 2 is larger than the effective detection distance D1, the microwave detecting module 10 is unable to detect the physiological signal of the human body 2, and thereby, the microwave detecting module 10 can be avoided from being mistakenly or carelessly activated form causing the far-infrared beam module 20 to irradiate the far-infrared beam L1.

It is noted that the range of the effective detection distance D1 can be varied and can be defined variously according to different physiological signals. For instance, the effective detection distance D1 can be ranged between 0~30 cm, that is, microwave detecting module 10 is able to detect the physiological signal of the human body 2 when it is located within 30 cm distance from the human body 2 and the microwave detecting module 10 is unable to detect the physiological signal of the human body 2 when it is located outside the 30 cm ranged away from the human body 2. Furthermore, when it is located inside the 30 cm distance from the human body 2, the microwave detecting module 10 can further be designed to detect the vascular pulsation when the distance between the microwave detecting module 10 and the human body 2 is between 10 cm and 15 cm, and when the distance between the microwave detecting module 10 and the human body 2 is larger than 15 cm but smaller than 30 cm, it is defined to detect heartbeat and respiration.

Figure 3:
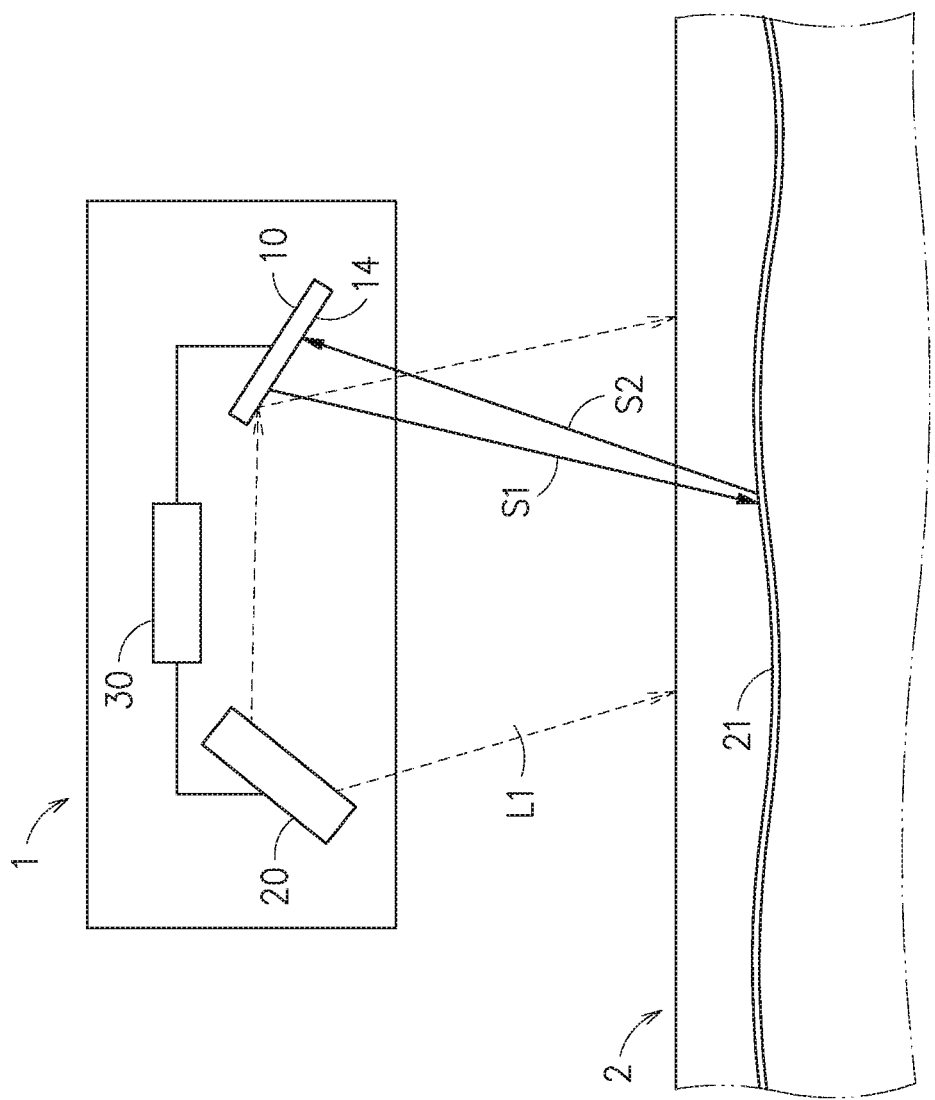
FIG. 3 is a schematic diagram showing a far-infrared emitter with physiological signal detection according to another embodiment of the present invention.

Please refer to FIG. 3, which is a schematic diagram showing a far-infrared emitter with physiological signal detection according to another embodiment of the present invention. In the embodiment shown in FIG. 1, all the far-infrared beam L1 is projected toward the human body 2. However, as shown in FIG. 3, the microwave detecting module 10 and the far-infrared beam module 20 can be arranged inclined by an angle with respect to the human body 2 while enabling the microwave detecting module to have a surface 14 that is made of a reflecting material, e.g. a metal, by which a portion of the far-infrared beam L1 is projected toward the surface 14 where it is reflected toward the human body 2 while the rest of the far-infrared beam L1 is projected directly toward the human body 2. As described in the above disclosure, the oscillating signal S1 is substantially a radio frequency signal that can be projected and cover the projection area of the far infrared beam L1 so as to modulate the physiological movement of the human body 2 while simultaneously reflecting a reflection signal S2 back to the microwave detecting module 10.

Figure 4:
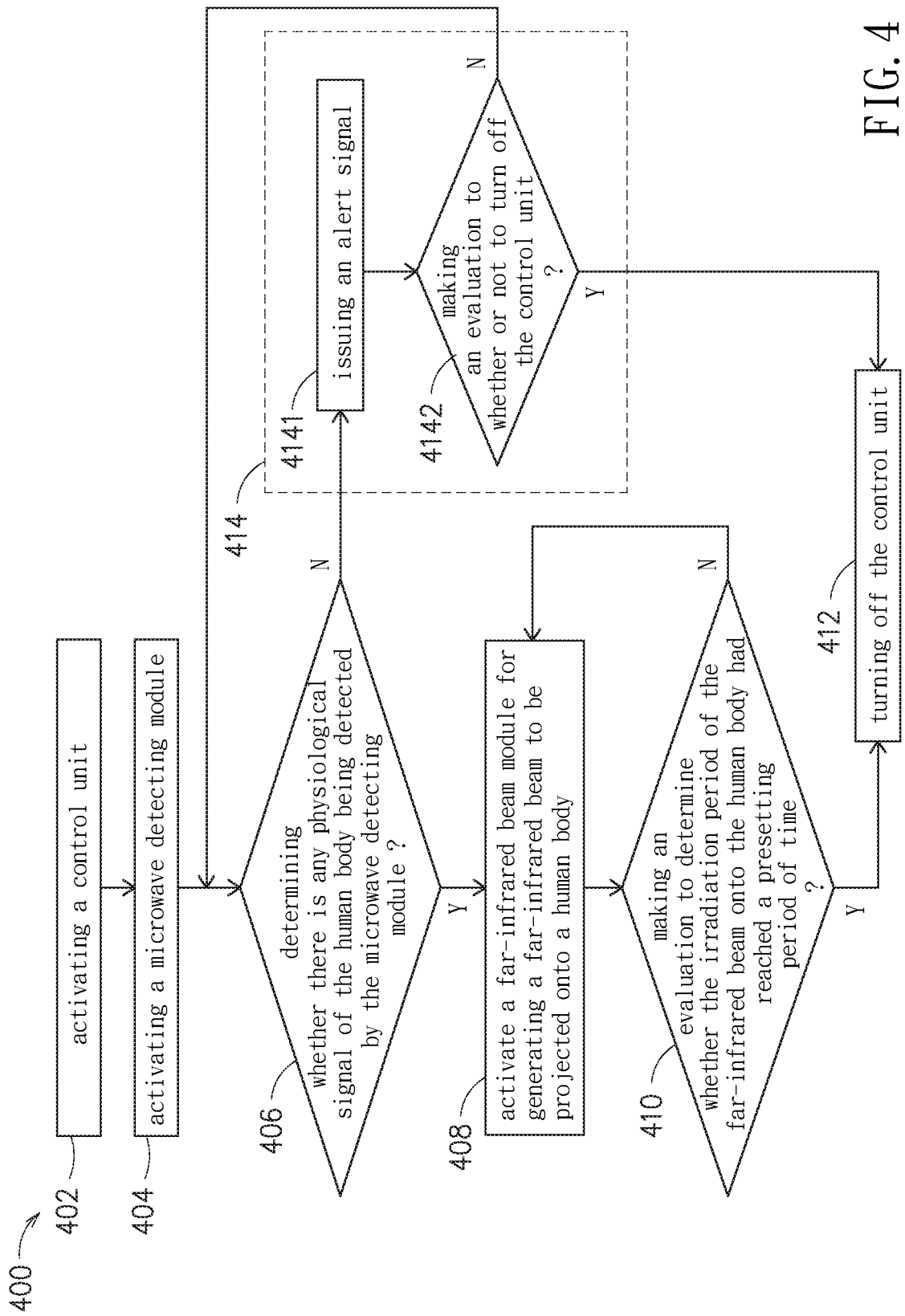
FIG. 4 is a flow chart depicting the steps performed in a method of operating the far-infrared emitter with physiological signal detection according to an embodiment of the present invention.

Please refer to FIG. 1 and FIG. 4, whereas FIG. 4 is a flow chart depicting the steps performed in a method of operating the far-infrared emitter with physiological signal detection according to an embodiment of the present invention. The method of operating the far-infrared emitter with physiological signal detection 400 comprises the following steps:

step 402: activating a control unit 30;
step 404: enabling the control unit 30 to activate a microwave detecting module 20 for enabling the microwave detecting module 20 to emit an oscillating signal S1 to a human body 2 so as to receive a reflection signal S2 reflected back from the human body 2 and thus to acquire a physiological signal of the human body 2 accordingly;
step 406: enabling the control unit 30 to determine whether there is any physiological signal of the human body being detected by the microwave detecting module 10; if so, the flow proceeds to step 408; otherwise, an alerting procedure 414 is being initiated;
step 408: enabling the control unit 30 to activate a far-infrared beam module 20 for generating a far-infrared beam L1 to be projected onto a human body 2 while enabling the microwave detecting module 10 to perform the detection of the physiological signal of the human body 2 continuously, and as soon as the microwave detecting module 10 is situated in a state that it is unable to detect any physiological signal of the human body 2, the alerting procedure 414 is being initiated;
step 410: enabling the control unit 30 to determine whether the irradiation period of the far-infrared beam L1 onto the human body 2 had reached a presetting period of time or not; if so, the flow proceeds to step 415; otherwise, the flow proceeds back to step 408 until the radiation period of the far-infrared beam L1 had reached the presetting period of time, whereas it is noted that the determination of the control unit 30 can be performed by a timer or a timing program installed in a cellular phone or a computer; and
step 412: turning off the control unit 30.

In addition, the alerting procedure 414 further comprises the following steps:

step 4141: enabling the control unit 30 to activate an alert unit to issue an alert signal; and
step 4142: making an evaluation to determine whether or not to turn off the control unit 30, whereas the evaluation perform in step 4142 can be made by a person that is being detected, i.e. the human body 2, or other persons; if so, the flow proceeds to step 412; otherwise, adjusting the position of the far-infrared emitter 20 with respect to the human body, and then enabling the flow to proceed back to step 406.

In the proceeding of the step 406 and 408, when the microwave detecting module 10 is situated in a state that it is unable to detect any physiological signal of the human body 2, the alert procedure 414 will be initiated. It is noted that there can be various reasons causing the microwave detecting module 10 to be unable to detect any physiological signal of the human body 2. For instance, when the microwave detecting module 10 is located at a location in a distance larger than the effective detection distance D1. However, such configuration can be beneficiary that when the distance between the microwave detecting module 10 and the human body 2 is larger than the effective detection distance D1, the microwave detecting module 10 is unable to detect the physiological signal of the human body 2, and thereby, the microwave detecting module 10 can be avoided from being mistakenly or carelessly activated form causing the far-infrared beam module 20 to irradiate the far-infrared beam L1.

To sum up, the present invention provides a far-infrared emitter with physiological signal detection and the method of operating the same, in that a microwave detecting module is integrated with a far-infrared beam module whereas the far-infrared beam module is designed to be activated according to the detection of physiological signal by the microwave detecting module that is designed under the guidance of a self-injection-locked oscillating principle, and thus the operation can be very energy efficient. Moreover, the irradiation time can be recorded while the physiological signals acquired during the irradiation can also be recorded and provided to the user as reference, by that the added value of the product is increased. In addition, the present invention can be designed to detect different physiological signals according to the difference in distance spaced between the human body and the device of the present invention, whereas the physiological signals can include vascular pulsation, heartbeat and respiration. Furthermore, since the microwave detecting module is highly sensitive, low cost and small in size, the whole device can be a wearable device that it is portable and can be easily fitted onto human body for medical purpose or home care services.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A far-infrared emitter with physiological signal detection, comprising:
    a microwave detecting module, further comprising: a self-injection-locked-state oscillating integrated antenna and a demodulator, for emitting an oscillating signal to a human body so as to receive a reflection signal reflected back from the human body and thus acquiring a physiological signal of the human body accordingly;
    a far-infrared beam module, for generating a far-infrared beam; and
    a control unit, electrically connected to the microwave detecting module and the far-infrared beam module, to be used for activating the microwave detecting module for detecting the physiological signal of the human body continuously while thereafter activating the far-infrared beam module to radiate the far-infrared beam onto the human body.

2. The far-infrared emitter of claim 1, wherein the self-injection-locked-state oscillating integrated antenna is further configured with an antenna and an active unit in a manner that the active unit is electrically connected to the antenna, and thereby, the antenna is enabled to perform a frequency selection operation while being enabled to oscillate with the active unit so as to generate the oscillating signal that is then to be transmitted to the human body by the antenna, and as soon as the corresponding reflection signal that is reflected back from the human body is received by the antenna, the self-injection-locked-state oscillating integrated antenna will be conditioned and locked into a self-injection-locked state while the oscillating signal is to be modulated into a frequency modulation/amplitude modulation signal according to a physiological sign of the human body; and moreover, the demodulator is electrically connected to the self-injection-locked-state oscillating integrated antenna and is used for receiving the frequency modulation signal/amplitude modulation signal and then demodulating the frequency modulation signal/amplitude modulation signal so as to acquire the physiological signal of the human body.

3. The far-infrared emitter of claim 2, wherein the demodulator further comprises:
    an envelope detector, for performing an amplitude demodulation operation upon the frequency modulation/amplitude modulation signal; and
    a differentiator, electrically connected to the self-injection-locked-state oscillating integrated antenna for receiving the frequency modulation signal/amplitude modulation signal to be used in a differential operation so as to convert the frequency modulation/amplitude modulation signal into an amplitude modulation signal, while the envelope detector is also electrically connected to the differentiator for enabling the envelope detector to perform an amplitude demodulation operation upon the amplitude modulation signal.

4. The far-infrared emitter of claim 1, wherein the microwave detecting module has a surface that is made of a reflecting material, by which a portion of the far-infrared beam is projected toward the surface where it is reflected toward the human body.

5. The far-infrared emitter of claim 4, wherein the surface is made of a metal.

6. The far-infrared emitter of claim 1, wherein all the far-infrared beam is projected toward the human body.

7. The far-infrared emitter of claim 1, wherein the microwave detecting module is arranged at an effective detection distance away from the human body while the effective detection distance is ranged between 0~30 cm; and when the distance between the microwave detecting module and the human body is within the range of the effective detection distance, the microwave detecting module is able to detect the physiological signal of the human body.

8. A method of operating the far-infrared emitter with physiological signal detection, comprising the steps of:
    (a) activating a control unit;
    (b) enabling the control unit to activate a microwave detecting module, which further comprises: a self-injection-locked-state oscillating integrated antenna and a demodulator, for enabling the microwave detecting module to emit an oscillating signal to a human body so as to receive a reflection signal reflected back from the human body and thus to acquire a physiological signal of the human body accordingly;
    (c) determining whether there is any physiological signal of the human body being detected by the microwave detecting module; if so, a flow proceeds to step (d); otherwise, an alerting procedure is being initiated;
    (d) enabling the control unit to activate a far-infrared beam module for generating a far-infrared beam to be projected onto a human body while enabling the microwave detecting module to perform the detection of the physiological signal of the human body continuously;
    (e) making an evaluation to determine whether the irradiation period of the far-infrared beam onto the human body had reached a presetting period of time or not; if so, the flow proceeds to step (f); otherwise, the flow proceeds back to step (d) until the radiation of the far-infrared beam had reached the presetting period of time; and
    (f) turning off the control unit.

9. The operating method of claim 8, wherein the alerting procedure further comprises the steps of:
    (c1) enabling the control unit to activate an alert unit to issue an alert signal; and
    (c2) making an evaluation to determine whether or not to turn off the control unit; if so, the flow proceeds to step (f); otherwise, adjusting the position of the far-infrared emitter with respect to the user, and then enabling the flow to proceed back to step (c).

10. The operating method of claim 9, wherein the evaluation performed in step (c2) is made by a person that is being detected or other persons.

11. The operating method of claim 8, wherein the evaluation performed in step (e) for determining whether the irradiation period of the far-infrared beam onto the human body had reached a presetting period of time is performed by a timer while the timer is activated by the control unit.

12. The operating method of claim 8, wherein when the microwave detecting module is unable to detect the physiological signal of the human body during the proceeding of step (d) and step (e), the alerting procedure is enabled.

13. The operating method of claim 8, wherein during the proceeding of step (c), the microwave detecting module is located within the range of an effective detection distance for allowing the microwave detecting module to detect the physiological signal of the human body; and the effective detection distance is ranged between 0~30 cm.

\* \* \* \* \*